US011854689B2

(12) United States Patent
Schaberg et al.

(10) Patent No.: US 11,854,689 B2
(45) Date of Patent: Dec. 26, 2023

(54) HEALTHCARE PERFORMANCE

(71) Applicant: CERNER INNOVATION, INC., Kansas City, KS (US)

(72) Inventors: Lisa Schaberg, Lee's Summit, MO (US); Don Jacob, Kansas City, KS (US); Nolan Howlett, Kansas City, KS (US); Shannon Robinson, Kansas City, KS (US); Tiffany Bateson, Kansas City, KS (US); Angela Betts, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 409 days.

(21) Appl. No.: 17/136,817

(22) Filed: Dec. 29, 2020

(65) Prior Publication Data
US 2022/0208359 A1    Jun. 30, 2022

(51) Int. Cl.
| G16H 50/20 | (2018.01) |
| G16H 10/20 | (2018.01) |
| G16H 40/20 | (2018.01) |
| G06Q 50/26 | (2012.01) |
| G06F 3/04842 | (2022.01) |

(52) U.S. Cl.
CPC .......... *G16H 40/20* (2018.01); *G06Q 50/265* (2013.01); *G06F 3/04842* (2013.01)

(58) Field of Classification Search
CPC .. G16H 40/20; G06Q 50/265; G06F 3/04842; G06F 3/0482
See application file for complete search history.

(56) References Cited

U.S. PATENT DOCUMENTS

| 11,348,679 | B1 * | 5/2022 | Perry | ..................... G16H 40/20 |
| 2018/0308584 | A1 * | 10/2018 | Prather | .................. G16H 10/60 |

* cited by examiner

*Primary Examiner* — Maroun P Kanaan
(74) *Attorney, Agent, or Firm* — KRAGULJAC LAW GROUP, LLC

(57) ABSTRACT

Systems, methods, and storage media useful in a healthcare computing platform to provide comprehensive safety measurement scores, and the individual safety measurements that make up the comprehensive safety measurement scores, for multiple hospitals in a geographic area and/or within a healthcare system are provided. Systems, methods, and storage media provided receive changes to individual safety measurements to model how changes to individual measurements impact the comprehensive safety measurement score for a hospital.

20 Claims, 9 Drawing Sheets

HEALTHCARE PERFORMANCE

BACKGROUND

A variety of performance and safety measures are gathered by surveys and using hospital data to calculate a composite safety measurement score for a hospital. Typically, composite safety measurement scores are developed by external safety rating agencies which are independent, non-profit organizations to provide transparency to the public to see how hospital is performing.

One of the most well recognized is the Leapfrog Group, which aggregates national performance measures from the Centers for Medicare & Medicaid Services (CMS). The Leapfrog Group is a national leader and advocate in hospital transparency. The Leapfrog Group is an independent, national not-for-profit organization founded more than a decade ago by the nation's leading employers and private health care experts.

A composite safety measurement score, such as Leapfrog, provides a single grade to represent a hospital's overall performance in keeping patients safe from preventable harm and medical errors. The composite safety measurement score recognizes the highest performing hospitals, identifies high-value care and educates consumers and employers when choosing a healthcare institution.

SUMMARY

This Summary is provided to introduce a selection of concepts in a simplified form that are further described below in the Detailed Description. This Summary is not intended to identify key features nor essential features of the claimed subject matter, nor is it intended to be used as an aid in determining the scope of the claimed subject matter. The present disclosure is defined by the claims as supported by the Specification, including the Detailed Description.

Systems, methods, and storage media provided are useful in a healthcare computing platform to provide comprehensive safety measurement scores, and the individual safety measurements that make up the comprehensive safety measurement scores for multiple hospitals in a geographic area and/or within a healthcare system.

Systems, methods, and storage media provided receive changes to individual safety measurements to model how changes to individual measurements impact the comprehensive safety measurement score for a hospital.

Although there are a number of services which provide a composite safety measurement score to a hospital, the composite safety measurement score is useful for patients and employers deciding on where to seek treatment but is difficult for the hospital or healthcare institution to analyze. It is difficult for hospitals or health institutions to determine how the score was calculated and where they should focus their efforts to improve their overall composite safety measurement score.

Embodiments of the present invention seek to assist hospitals and other healthcare institutions on improving their overall composite safety measurement score. Embodiments of the present invention analyze the composite safety measurement score to determine the individual safety measurements making up the composite safety measure score. Embodiments break down the composite safety measurement score by hospital and hospital system as well as by geographic location. Modeling module of the present invention provides a tool for leaders to model how improvements (or deteriorations) of one or more individual safety measurements impact the composite safety measure score. This allows leaders to identify the critical path and high impact measurements to improve their overall composite safety measure score. The modeling module assists hospital with a program for developing, executing and improving their comprehensive safety measure score.

BRIEF DESCRIPTION OF THE DRAWINGS

Illustrative aspects of the present invention are described in detail below with reference to the attached drawing figures, and wherein.

DETAILED DESCRIPTION

Figure 1:
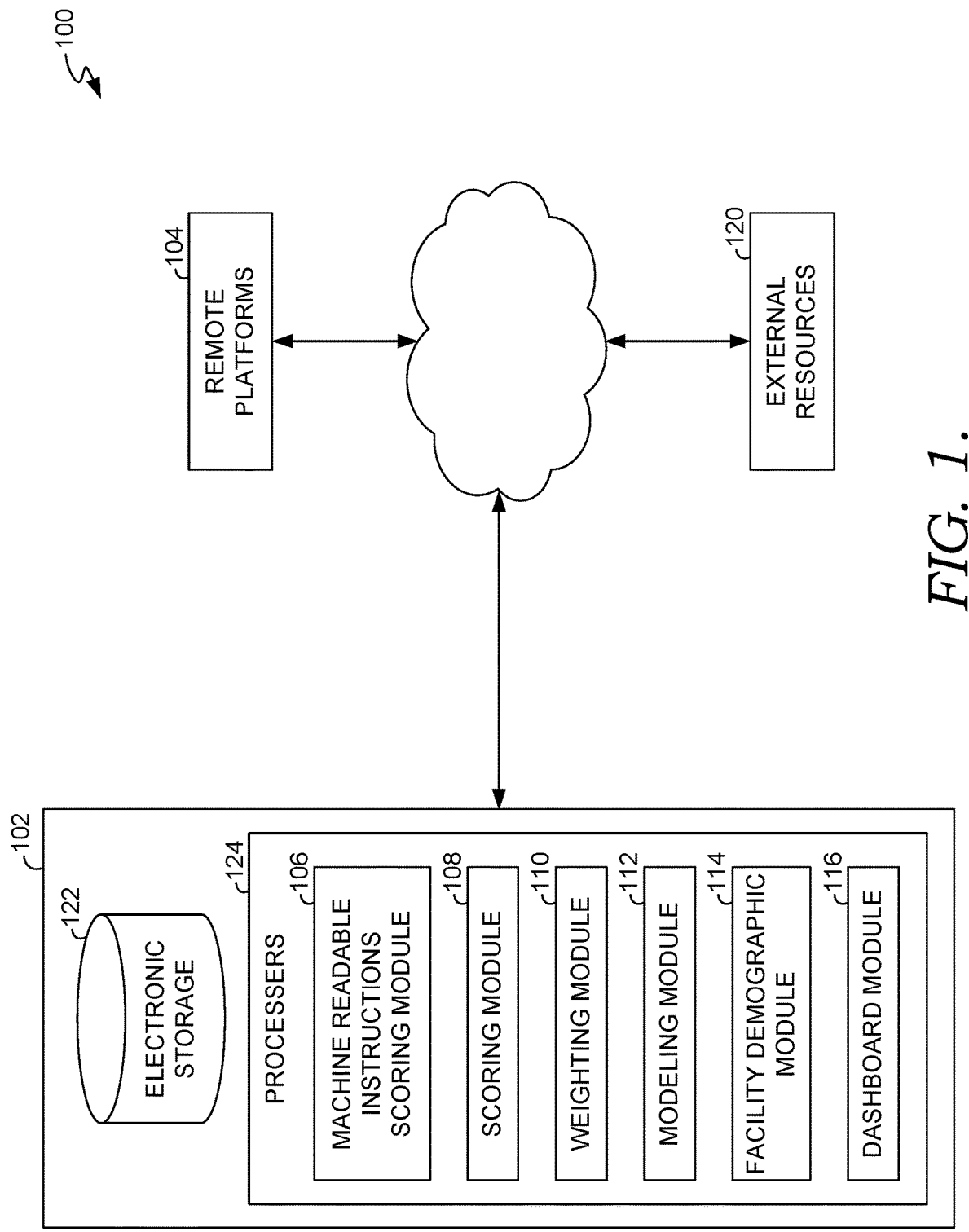
FIG. 1 illustrates a healthcare computing platform, in accordance with aspects of the invention.

The subject matter of the present invention is being described with specificity herein to meet statutory requirements. However, the description itself is not intended to limit the scope of this patent. Rather, the inventors have contemplated that the claimed subject matter might also be embodied in other ways, to include different operators or combinations of operators similar to the ones described in this document, in conjunction with other present or future technologies. Terms should not be interpreted as implying any particular order among or between various operators herein disclosed unless and except when the order of individual operators is explicitly described. As such, although the terms "operator" and/or "block" can be used herein to connote different elements of system and/or methods, the terms should not be interpreted as implying any particular order and/or dependencies among or between various components and/or operators herein disclosed unless and except when the order of individual operators is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

The healthcare computing platform of embodiments of the invention assists healthcare hospitals and systems by providing a platform to break down a composite safety measurement score into data that can be used by the hospital or hospital system to see individual safety measurement scores, weighting, and hospital demographic information. The platform further allows hospitals to compare their composite safety measurement scores to certain hospitals in a specific geographic location. Furthermore, the platform allows a leader at a hospital system to view the comprehensive safety measurement scores across the hospital system as well as view and compare multiple hospitals.

Along with providing a comprehensive dashboard to leaders to view and compare scores by geographic location and system, the platform provides a modeling tool for a leader to model how improving individual safety measurements will impact the comprehensive safety measurement score for a particular hospital. The individual safety measurements that are evaluated to calculate the comprehensive safety measurement score include, but are not necessarily limited to, inpatient injuries, infections, medical and medication errors, central line-associated bloodstream infections, catheter-associated urinary tract infections, surgical site infections for colon surgery, MRSA and *C. difficile* infections, falls and trauma, very severe pressure injuries, preventable complications from surgery such as foreign objects retained in the body and accidental punctures or lacerations, strong nursing leadership and engagement, computerized physician order entry systems to prevent medication errors, safe medication administration, hand hygiene policies and the right staffing for the ICU.

Typically the individual safety measurements are publicly available but may also be obtained by patient surveys or hospital reported information. The individual safety measurements may include objective (e.g., hospital acquired infection rate) and subjective (e.g., patient rating of physician communication). Currently, the comprehensive safety measurement score for Leapfrog looks to 28 individual safety measurements for a hospital. It will be appreciated that some of these individual safety and quality measurements may change as new information is learned and healthcare treatment evolves.

The modeling module provides the information for each hospital to identify where improvements in safety need to be made within a particular hospital. The modeling module allows the leader to determine where best to focus time and efforts on improving the hospital's comprehensive safety measurement score. Based on modeling performed by the module, a leader will be able to identify improvements to individual safety measures that will have a high impact on the overall comprehensive safety measurement score that are relatively simple to implement. For example, a leader may decide to focus efforts on objective measures, such as reducing falls and hospital acquired infections.

The platform may be used by different hospitals and hospital systems, further allowing an improvement in healthcare agnostic to the electronic health record system used by the hospital or hospital system. The platform provides a data driven, programmatic approach to improving safety in hospitals. Data is automatically abstracted from the comprehensive safety measurement score and the platform provides a single source for a hospital leader to view and analyze data for the comprehensive safety measurement score. Previous efforts to manually collect and collate data from the non-profit for the comprehensive safety measurement score took months, was incomplete and was prone to error. As the comprehensive safety measurement score is typically published twice a year, with changes to the individual safety measurements and assigned weights, manual collection and collation is not feasible. Furthermore, there is no way to model individual safety improvements and their impact on the comprehensive safety measurement score for the hospital. The platform of embodiments of the present invention collects and collates the data in a matter of hours and provides it to leaders who can immediately begin making improvements to patient safety.

FIG. 1 illustrates a system configured to be useful in a computer healthcare system to consume clinical quality language queries in a programmatic manner, in accordance with one or more implementations. In some implementations, system may include one or more healthcare cloud computing platforms 102. Computing platform(s) 102 may be configured to communicate with one or more remote platforms 104 according to a client/server architecture, a peer-to-peer architecture, and/or other architectures. Remote platform(s) 104 may be configured to communicate with other remote platforms via computing platform(s) 102 and/or according to a client/server architecture, a peer-to-peer architecture, and/or other architectures. Users may access system 100 via remote platform(s) 104.

In some implementations, computing platform(s) 102, remote platform(s) 104, and/or external resource(s) 120 may be operatively linked via one or more electronic communication links. For example, such electronic communication links may be established, at least in part, via a network, such as the Internet and/or other networks. It will be appreciated that this is not intended to be limiting, and the scope of this disclosure includes implementations in which computing platform(s) 102, remote platform(s) 104, and/or external resource(s) 120 may be operatively linked via some other communication media.

A given remote platform 104 may include one or more processors configured to execute computer program modules. The computer program modules may be configured to enable an expert or user associated with the given remote platform 104 to interface with system 100 and/or external resource(s) 120, and/or provide other functionality attributed herein to remote platform(s) 104. By way of non-limiting example, a given remote platform 104 and/or a given computing platform 102 may include one or more of a server, a desktop computer, a laptop computer, a handheld computer, a tablet computing platform, a NetBook, a Smartphone, a gaming console, and/or other computing platforms.

External resources 120 may include sources of information outside of system 100, external entities participating with system 100, and/or other resources.

Computing platform(s) 102 may include electronic storage 122, one or more processors 124, and/or other components. Computing platform(s) 102 may include communication lines, or ports to enable the exchange of information with a network and/or other computing platforms. Illustration of computing platform(s) 102 in FIG. 1 is not intended to be limiting. Computing platform(s) 102 may include a plurality of hardware, software, and/or firmware components operating together to provide the functionality attributed herein to computing platform(s) 102. For example, computing platform(s) 102 may be implemented by a cloud of computing platforms operating together as computing platform(s) 102.

Electronic storage 122 may comprise non-transitory storage media that electronically stores information. The electronic storage media of electronic storage 122 may include one or both of system storage that is provided integrally (i.e., substantially non-removable) with computing platform(s) 102 and/or removable storage that is removably connectable to computing platform(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from computing platform(s) 102, information received from remote platform(s) 104, and/or other information that enables computing platform(s) 102 to function as described herein.

Processor(s) 124 may be configured to provide information processing capabilities in computing platform(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device or processor(s) 124 may represent processing functionality of a plurality of devices operating in coordination. Processor(s) 124 may be configured to execute modules 108, 110, 112, 114, and/or 116, and/or other modules. Processor(s) 124 may be configured to execute modules 108, 110, 112, 114, and/or 116, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 108, 110, 112, 114, and/or 116 are illustrated in FIG. 1 as being implemented within a single processing unit, in implementations in which processor(s) 124 includes multiple processing units, one or more of modules 108, 110, 112, 114, and/or 116 may be implemented remotely from the other modules. The description of the functionality provided by the different modules 108, 110, 112, 114, and/or 116 described below is for illustrative purposes, and is not intended to be limiting, as any of modules 108, 110, 112, 114, and/or 116 may provide more or less functionality than is described. For example, one or more of modules 108, 110, 112, 114, and/or 116 may be eliminated, and some or all of its functionality may be provided by other ones of modules 108, 110, 112, 114, and/or 116. As another example, processor(s) 124 may be configured to execute one or more additional modules that may perform some or all of the functionality attributed below to one of modules 108, 110, 112, 114, and/or 116.

Computing platform(s) 102 may be configured by machine-readable instructions 106. Machine-readable instructions 106 may include one or more instruction modules. The instruction modules may include computer program modules. The instruction modules may include one or more of scoring module 108, weighting module 110, modeling module 112, facility demographic module 114, and dashboard module 116, and/or other instruction modules.

Scoring module 108 is configured to obtain comprehensive safety measurement scores from an external resource 120. For example, scoring module 108 automatically obtains comprehensive safety measurement scores for hospitals from an external safety rating agency, such as the Leapfrog Group. It will be appreciated that a comprehensive safety measurement score may be obtained from any external safety rating agency and utilized with platform 102.

Scoring module 108 may be scheduled to contact external resources 120 to determine if there is any new information or may communicate when new information is expected to be published. For example, Leapfrog Group publishes comprehensive safety measurement scores for hospitals twice a year. Once the comprehensive safety measurement scores are published for a given period of time, platform 102 downloads the comprehensive safety measurements for each hospital along with any associated metadata.

The individual safety measurements and weighting are applied to each hospital for the same reporting period to equally compare the safety of different hospitals. However, the safety measurements and weighting are not the same for each reporting period. For example, the individual safety measurements and weighting for Spring 2021 will often be different from the individual safety measurement and weighting for Fall 2021. As new information is learned about healthcare safety, changes are made by the external safety rating agency to account for new information. It will be appreciated that the reporting periods may vary and may be monthly, twice a year, or yearly depending on the comprehensive safety measurement score analyzed by platform 102.

Once scoring module 108 has obtained the comprehensive safety measurement scores and associate metadata for one or more of the hospitals, the scoring module 108 analyzes the metadata associated with the comprehensive safety measurement scores for that time period to determine the individual safety measurements that make up the comprehensive safety measurement score obtained from external resource 120 for the given time period. Typically, the comprehensive safety measurement score is made of multiple individual safety measurements described above. Scoring module 108 determines the hospital identifier from the metadata associated with each comprehensive safety measurement score. Scoring module 108 stores in electronic storage 122 the comprehensive safety measurement score for each hospital identifier. Scoring module 108 stores in electronic storage 122 the individual safety measurements that were used to calculate the comprehensive safety measurement score along with the reporting period.

Weighting module 110 is configured to determine the weighted value for each of the individual safety measurements that make up the comprehensive safety measurement score by analyzing the metadata associated with the comprehensive safety measurement score. For example, if the comprehensive safety measurement score is calculated from twenty individual measurements, some or all of these measurements have a weight associated. This weighting changes each reporting period. Weighting module 110 stores in electronic storage 122 the weighting for each of the individual safety measurements determined by scoring module 108.

Facility demographic module 114 is configured to determine demographic data for each of the hospitals with a comprehensive safety measurement score. In one embodiment, facility demographic module 114 parses geographic information from the metadata associated with the comprehensive safety measurement scores and applies geocoding to the facility and its location. In an alternative embodiment, using the hospital identifier, facility demographic module 114 accesses a data table for geocoding in electronic storage 122 to match the facility to its geographic location. Additionally, facility demographic module 114 compares the hospital identifier to a data table to determine if the hospital is part of a larger hospital system. For example, using a database mapping hospitals to hospital systems, such as DEFINITIVE, hospitals across the nation are mapped to their large hospital system. For each hospital with a comprehensive safety measurement score, facility demographic module 114 stores in electronic storage 122 the hospital identifier, geocoding for the hospital and associated hospital system.

Dashboard module 116 is configured to access the data stored in electronic storage 122 by scoring module 108, weighting module 110, and facility demographic module 114 to display a variety of information to leaders regarding safety performance for each hospital further delineated by geographic region, hospital system, and comprehensive safety measurement score group (e.g., A, B, C, D, F scores).

Figure 5A:
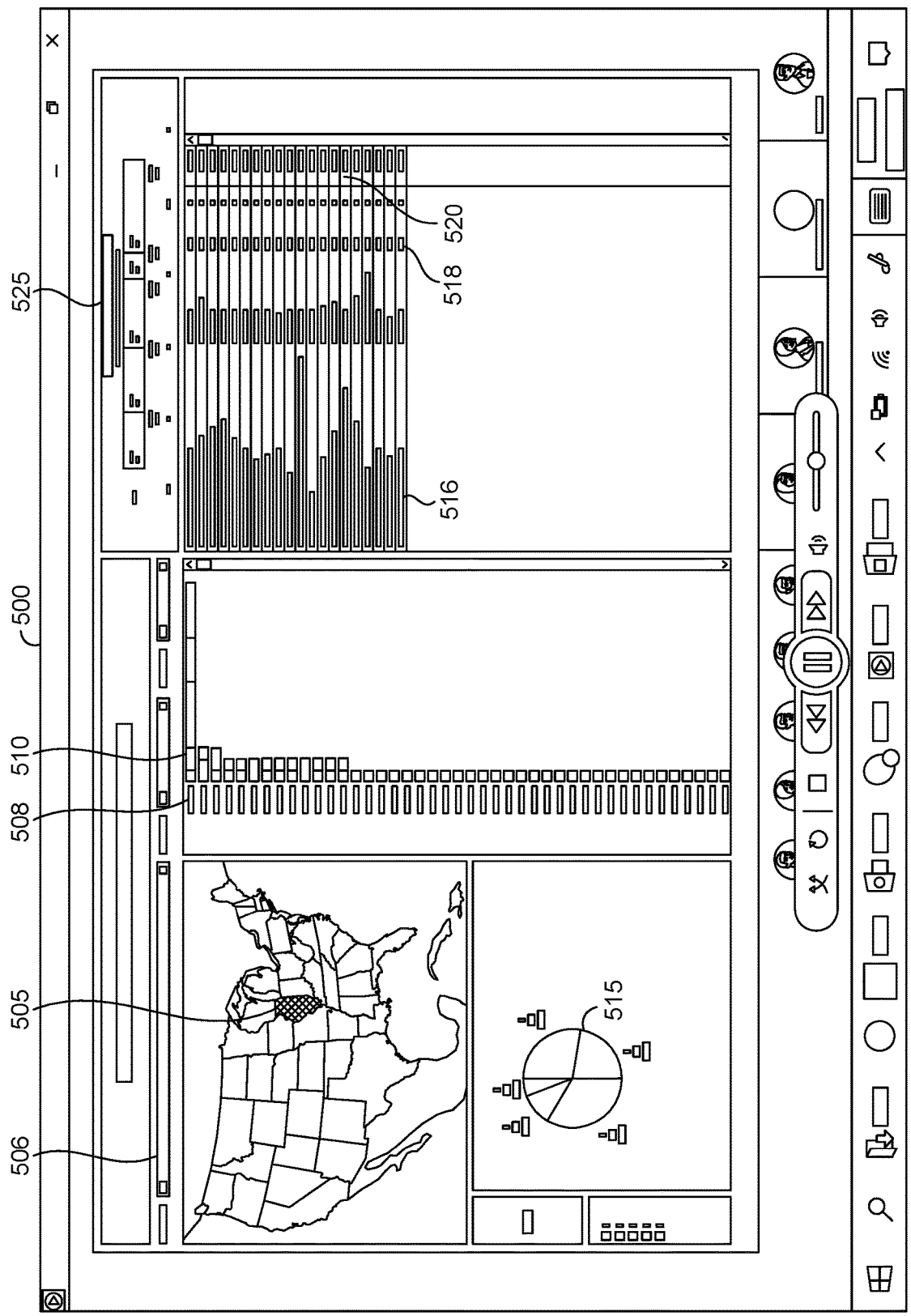
FIGS. 5A-5C depict exemplary graphical user interfaces of comprehensive safety measure scores broken down by geographic regions, hospitals, and hospital systems.
Figure 5B:
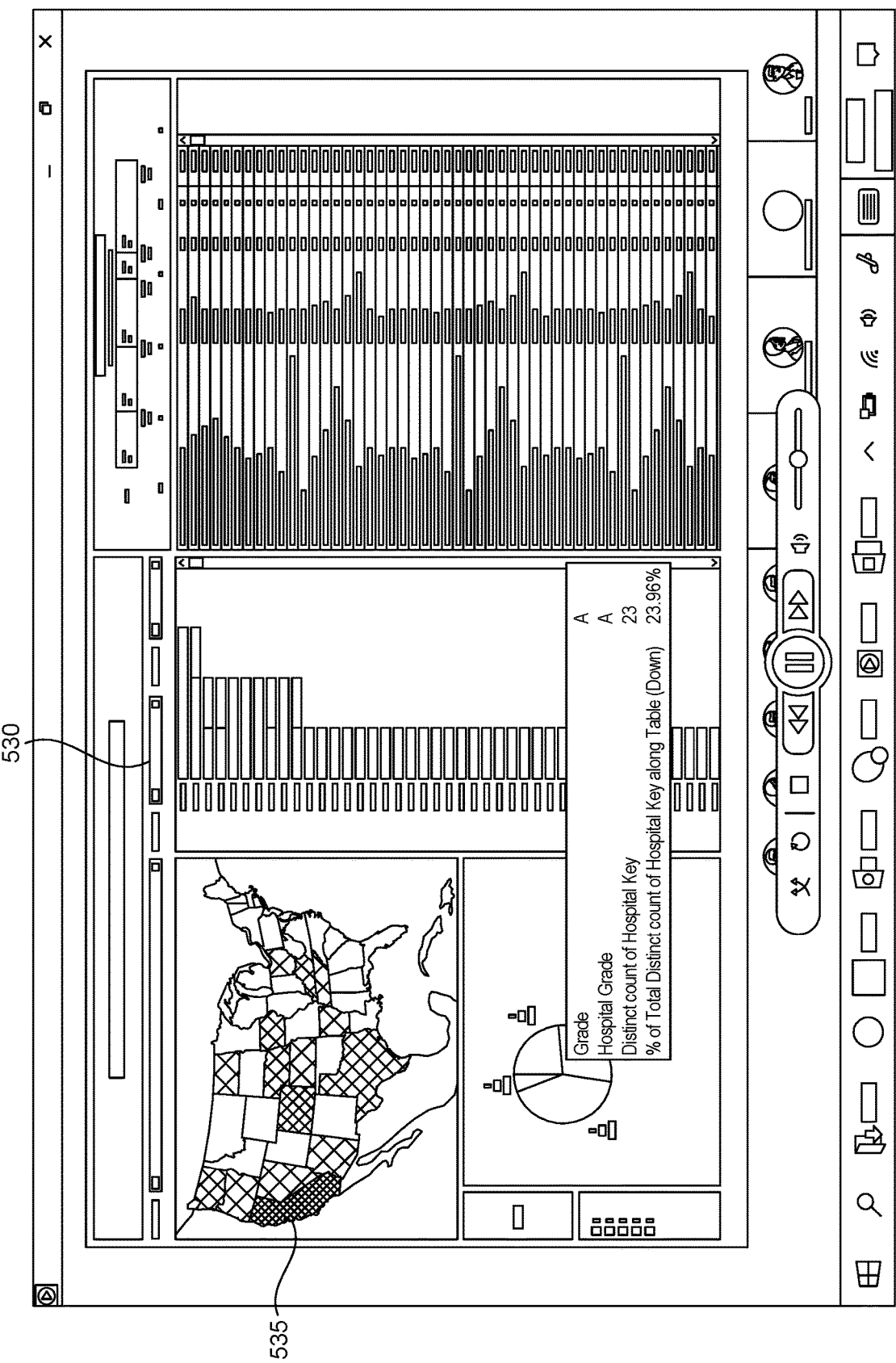
Figure 5C:
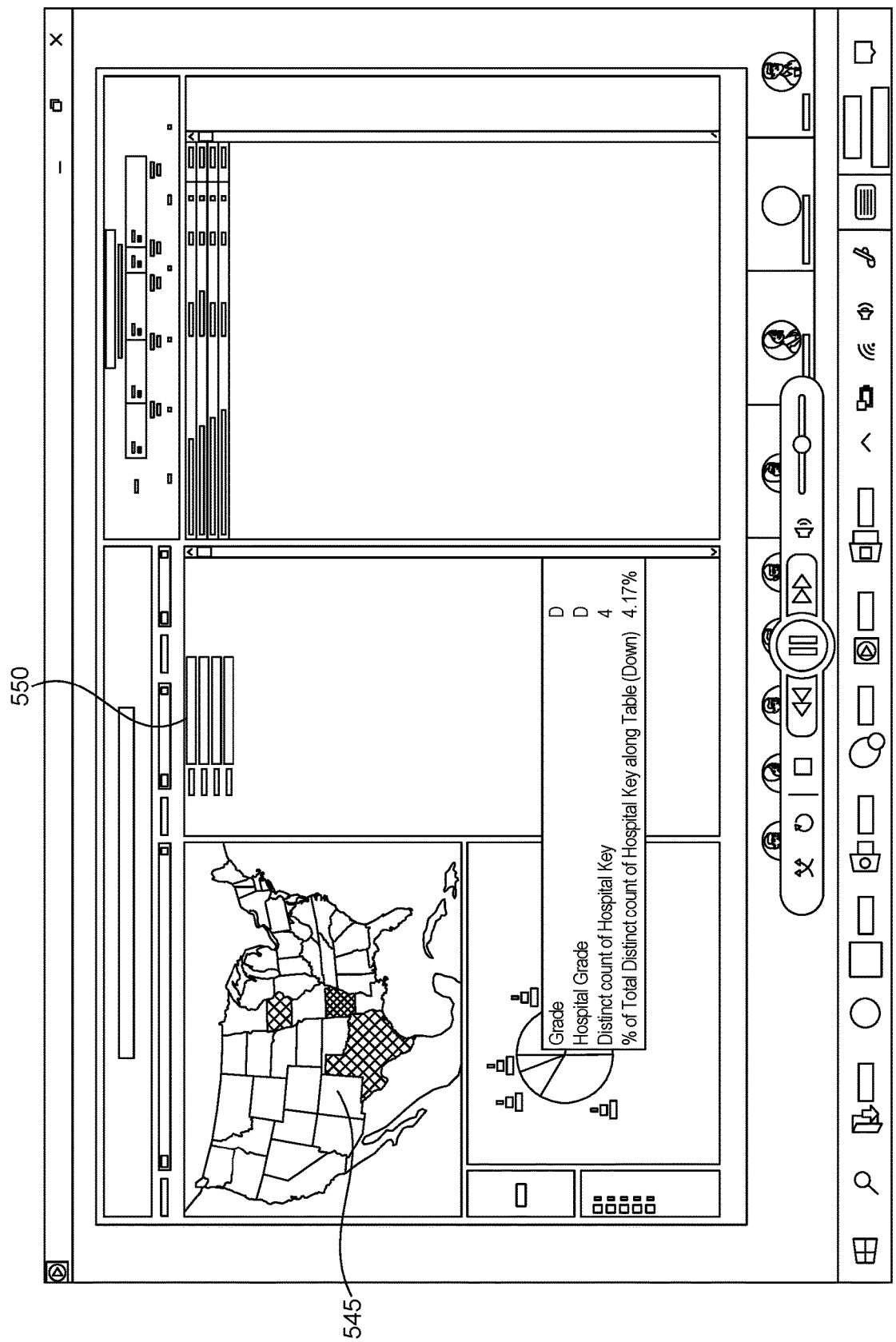

With reference to FIGS. 5A-5C, an exemplary healthcare performance dashboard 500 is shown.

Dashboard module 116 is configured to display some or all of hospitals and the comprehensive safety measurement score for each hospital. In one embodiment, the comprehensive safety measurement score received by the scoring module 108 from the external resource 120 (health safety agency) is expressed as a letter grade A, B, C, D, and F, without a numerical representation. Platform 102 leverages the individual safety measurements and weight information stored from the metadata for the comprehensive safety measurement score to calculate a numeric value for the letter grade for each hospital. In its communications, the healthcare safety agency 120 only provides the letter grade to leaders and not an associated numeric value. This makes it difficult for leaders to determine how close they are to improving a letter grade for a particular hospital. For example, a hospital may close to an A letter grade but have a B grade only to have missed the A grade by a very small amount. A hospital leader would not be able to tell this from just the letter grade provided by the healthcare safety agency.

Utilizing platform 102, as shown in FIG. 5A, dashboard 500 displays the letter grade 518, associated numeric grade 520, and ledger 525 showing the numeric range for the letter grade (for the specified reporting period) for hospitals 516 having a comprehensive safety measurement score obtained by scoring module 108. Leaders can view the numeric score 520 on dashboard module 116, along with a ledger 525 showing the numeric range for each letter grade, to see numerically how far a score is improving (or moving down) a letter grade for each hospital 516.

In one embodiment, the dashboard 500 provides an interactive map 505, where a user can select a geographic area, such as a state, city, or region, to find data regarding comprehensive safety measurement scores for hospitals in that geographic location. The hospitals in the selected geographic location 505 are further broken down into regions 508 (cities or within a number of miles) displaying how many hospitals 510 within that region are within particular composite safety measurement score bands (A, B, C, D, F). This allows a hospital leader to see how other hospitals scored within the region and what composite safety measurement scores the leader's hospital is competing with for patients. The health safety agency does not provide the ability to view numeric scores and compare grades against other facilities in a geographic region.

Dashboard module 116 provides a view for a leader of hospitals that are part of a hospital system 530 as shown in FIG. 5B. As described above, platform 102 can associate hospital identifiers with the correct hospital system membership. Dashboard module 116 aggregates comprehensive safety measurement scores for hospitals within the hospital system in an easy to read format. For example, Hospital System A is located in multiple states and region 535 throughout the United States.

With reference to FIG. 5C, a leader for a hospital system can further drill down and select particular regions 545 to view comprehensive safety measurement scores for hospitals 550 within the hospital system within the region. For example, Hospital System A 530 can view comprehensive safety measurement scores for all hospitals within California 535. The dashboard module 116 then breaks down the hospitals for the hospital system within particular comprehensive safety measurement score bands (A, B, C, D, F) within that region. This allows a hospital system leader to see how hospitals within the system within the region are benchmarking against one another. The health safety agency does not provide the ability to view a breakdown of hospitals by hospital system.

Figure 6:
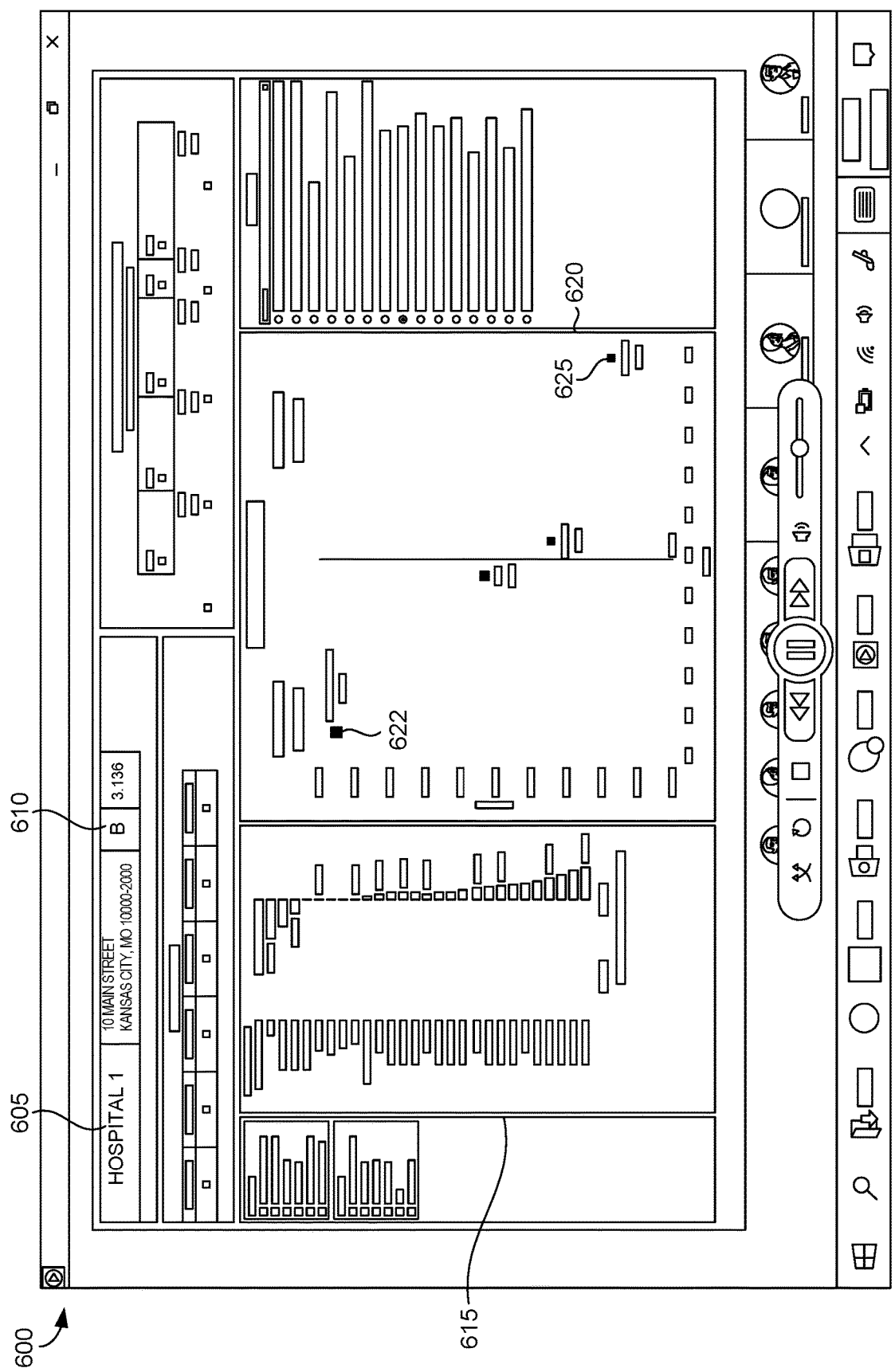
FIG. 6 depicts exemplary graphical user interfaces for displaying how improvements (or deteriorations) of one or more individual safety measures impact the composite safety measure score.

With reference to FIG. 6, dashboard module 116 displays a graphical user interface 600 with the individual safety measurements 615 and scores for each individual safety measurement for a hospital 605. Dashboard module 116 displays the comprehensive safety measurement score 610 as both a letter grade and a numeric grade 610.

Decision matrix 620 of graphical user interface plots individual safety measurements accordingly with the X axis being the percent impact the individual safety measurement has on the comprehensive safety measurement score and the Y axis being the effort needed to change the individual safety measurement. The individual safety measurements on the left top of the decision matrix represent opportunities to focus efforts to improve comprehensive safety measurement scores. These are opportunities to quickly improve a hospital's comprehensive safety measurement score.

In one embodiment, the effort needed to change the individual safety measurement is measured by the existence of programmatic safety programs, oftentimes in nursing, that can be implemented for an objective individual safety measurement (e.g., falls prevention, infection control) 622 while the effort to improve communication of physicians 625 is a subjective individual safety measurement and may be more difficult to implement. The objective individual safety measurements are often nursing driven, a leader may have a larger opportunity to impact nursing and make significant changes to safety in 12-16 weeks, before the next reporting period for the comprehensive safety measurement score.

Decision matrix 620 is user interactive and can be used with modeling module 112 to change and view how change to one or more individual safety measurements can impact the comprehensive safety measurement performance score for a hospital.

Figure 7:
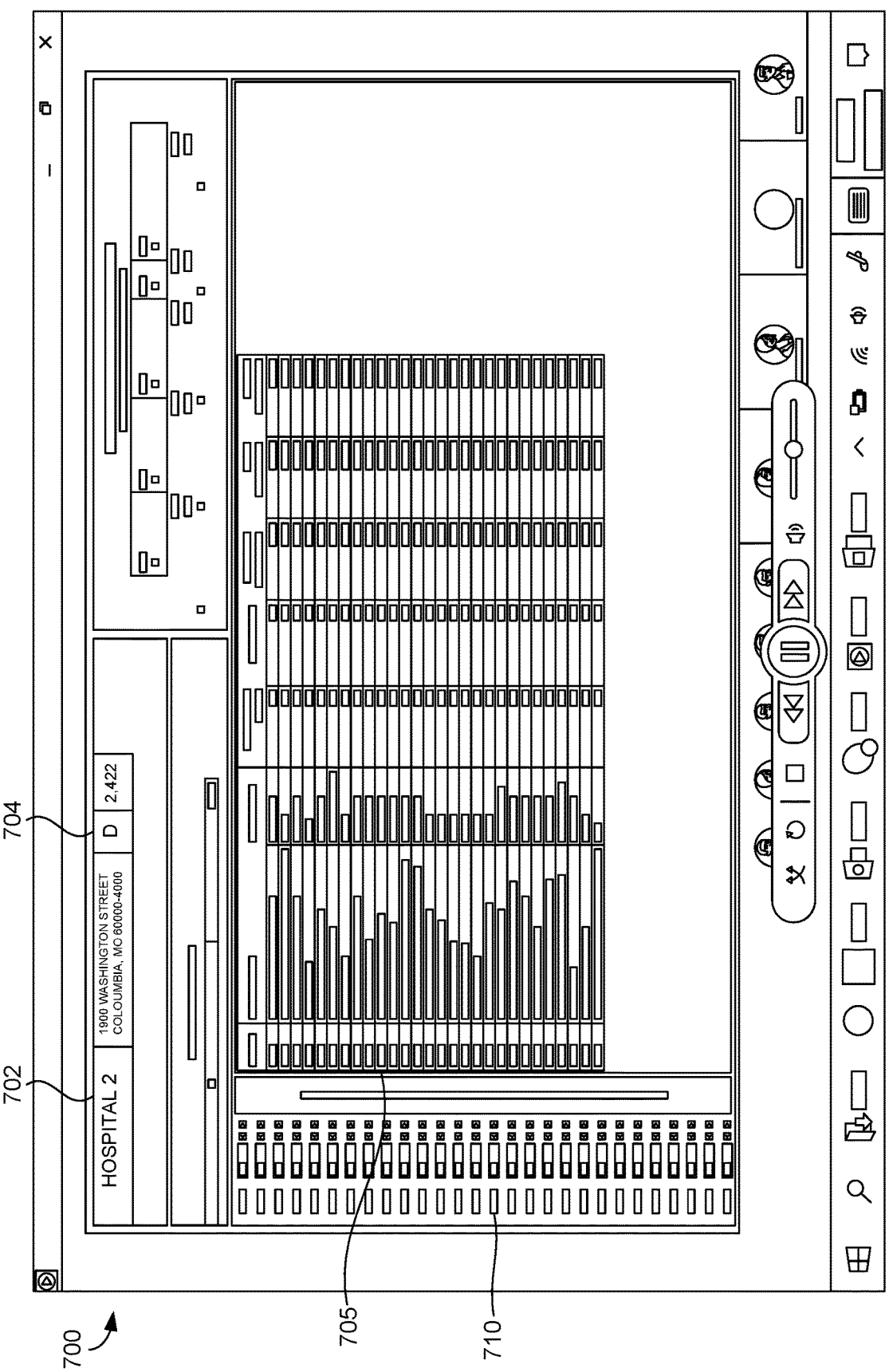
FIG. 7 depicts an exemplary graphical user interface to model how improvements (or deteriorations) of one or more individual safety measures impact the composite safety measure score.

Modeling module 112 is configured to model how changes in individual safety measurements would impact a hospital's comprehensive safety measurement score. As can be seen in FIG. 7, a graphical user interface 700 is shown with the individual safety measurements 705 that make up the comprehensive safety measurement score 704 for Hospital 2 702. Modeling module 112 receives proposed changes to values of one or more of the individual safety measurements through change field 710 or via decision matrix 625 of FIG. 6. The modeling module 112 receives the proposed changes to one or more of the individual safety measurements, applies the weighting criteria determined by weighting module 110 to each of the individual safety measurements to calculate a proposed/predicted comprehensive safety measurement score. For example, the modeling module 112 would change comprehensive safety measurement score 704 for Hospital 2 702 from a D (2.422) to a C (2.6) if the individual safety measurement for "falls" were improved for Hospital 2 by 10% from its current value and the individual safety measurement for "hospital acquired infections" were improved by 5% from its current value.

Modeling module 112 may be used on data historically and prospectively. The comprehensive safety measurement scores, individual safety measurements, weighting, geographic information and hospital information is stored electronic storage 122 for each reporting period so that it is accessible to leaders from platform 102. Modeling module 112 provides a data-driven picture of how changes to individual safety measurements will change the comprehensive safety measurement score for a hospital and hospital system. It may be that Hospital 2 will see a greater improvement of its comprehensive safety measurement score by focusing on preventing *C. difficile* infections instead of making incremental improvements to preventing MRSA. It allows for leaders to have a broad view of the data and develop long term view to improve quality of care the hospital.

Figure 2:
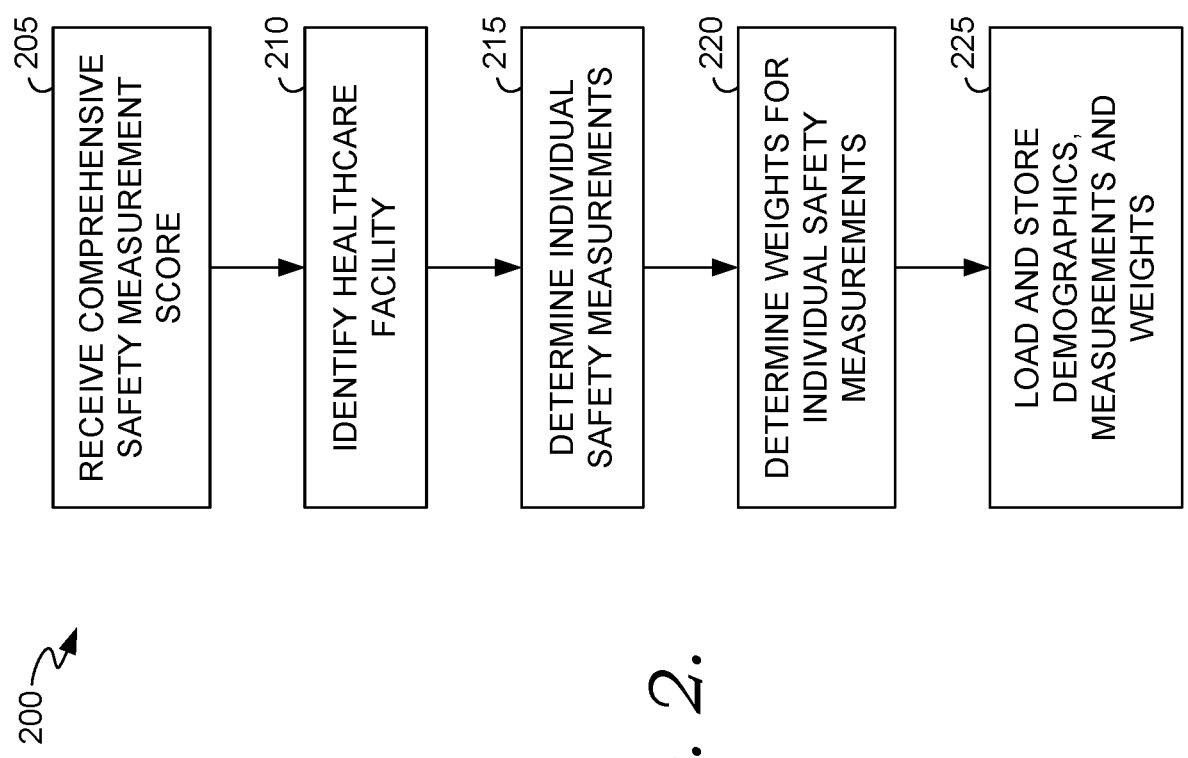
FIG. 2 depicts a flow chart of analyzing individual safety measurements and demographics for a comprehensive safety measure score in accordance with aspects of the invention.

FIG. 2 illustrates a method useful in a computing platform 102, in accordance with one or more implementations. With reference to FIG. 2, operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not necessarily limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

FIG. 2 illustrates method 200, in accordance with one or more implementations. Method 200 may be performed by one or more hardware processors configured by machine-readable instructions, including a module that is the same as or similar to scoring module 108, weighting module 110, and facility demographic module 114 in accordance with one or more implementations.

Operation 205 receives comprehensive safety measurement scores from a comprehensive safety measurement scores for multiple hospitals from an external safety rating agency, such as the Leapfrog Group, for a given time period. Operation 210 identifies each of the multiple hospitals for which there are comprehensive safety measurement scores. This is done by analyzing metadata associate with the comprehensive safety measurement scores for hospital identifiers. Operation 210 determines the geographic location of each hospital with a comprehensive safety measurement score and if each hospital is a member of a larger hospital system. Operation 215 determines the individual safety measurements that have been utilized to calculate the comprehensive safety measurement scores. The same individual measurements are utilized for all hospitals to provide objective comprehensive safety measurements scores and to allow consumers to compare the safety and care of different hospitals. Typically, multiple individual safety measurements are utilized to calculate the comprehensive safety measurement scores and are described in more detail above.

Operation 220 determines the weight for each of the multiple individual safety measurements. For example, the individual safety measurement for preventing hospital acquired infections may be weighted more heavily than individual safety measurements related to staffing policies. Operation 225 loads and stores the comprehensive safety measurement scores for the multiple hospitals, individual safety measurements, weights, geographic, and hospital system information in electronic storage 122 to be leverage by dashboard module 116 and modeling module 112.

Figure 3:
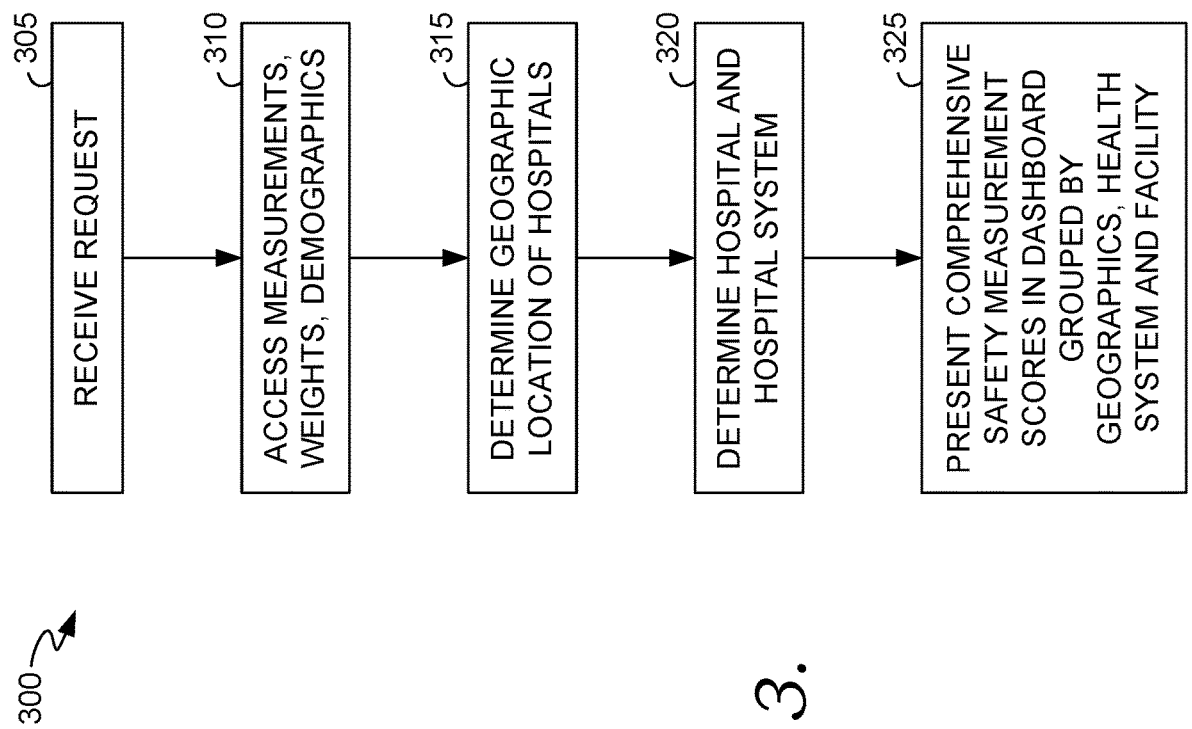
FIG. 3 depicts a flow chart of presenting on a graphical user interface comprehensive safety measure scores grouped by demographics in accordance with aspects of the invention.

FIG. 3 illustrates a method useful in a computing platform 102, in accordance with one or more implementations. With reference to FIG. 3, operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not necessarily limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

FIG. 3 illustrates method 300, in accordance with one or more implementations. Method 300 may be performed by one or more hardware processors configured by machine-readable instructions including a module that is the same as or similar to dashboard module 116 in accordance with one or more implementations.

Operation 305 receives a request from a user, such as a hospital leader, to view the comprehensive safety measurement scores and related information for multiple hospitals for a given time period using platform 102. Operation 305 may specify the safety agency for the comprehensive safety measurement scores or it may be defaulted to user preference. Operation 310 accesses the comprehensive safety measurements scores, individual safety measurements, weights, geographic, and hospital system information stored in electronic storage 122.

Operation 315 determines the geographic location of the hospitals having comprehensive safety measurement scores and operation 310 determines the hospital systems for hospitals having comprehensive safety measurement scores. As shown in FIGS. 5A-5C, operation 325 causes a user-interactive graphical user interface to display the comprehensive safety measurement scores by geographic location and hospital system at the user's request. Operation 325 can also display the individual safety measurements and weights via a user-interactive graphical user interface.

Figure 4:
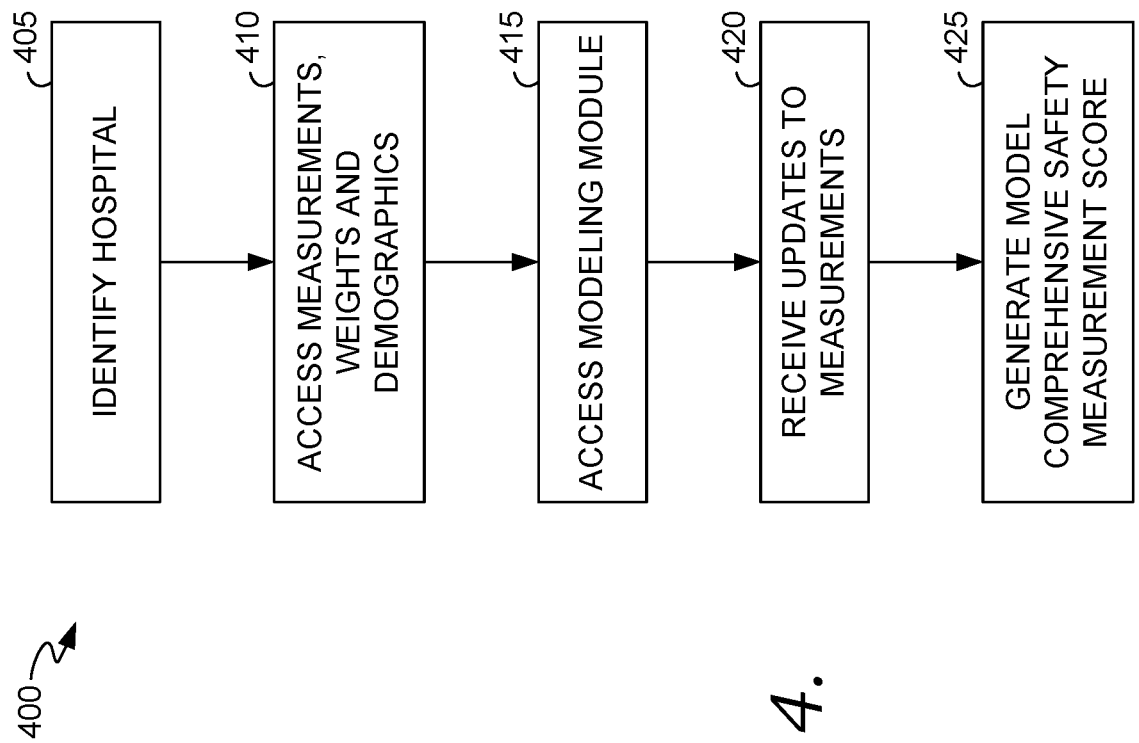
FIG. 4 depicts a flow chart of modeling the impact on a comprehensive safety measure score of changes to individual safety measurements in accordance with aspects of the invention.

FIG. 4 illustrates a method useful in a computing platform 102, in accordance with one or more implementations. With reference to FIG. 4, operations of method 400 presented below are intended to be illustrative. In some implementations, method 400 may be accomplished with one or more additional operations not described, and/or without one or more of the operations discussed. Additionally, the order in which the operations of method 400 are illustrated in FIG. 4 and described below is not necessarily limiting.

In some implementations, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 200.

FIG. 4 illustrates method 400, in accordance with one or more implementations. Method 400 may be performed by one or more hardware processors configured by machine-readable instructions, including a module that is the same as or similar to modeling module 112 in accordance with one or more implementations.

Operation 405 receives identification of a hospital with a comprehensive safety measurement score for a given time period. For example, a hospital leader selects to view the comprehensive safety measurement score and related information for Hospital A. Operation 410 accesses the comprehensive safety measurement score, individual safety measurements, and weights from electronic storage 122.

Operation 415 accesses the modeling module and provides a user interactive graphical user interface to a user to input changes to individual safety measurements to model the impact on the comprehensive safety measurement score for the selected hospital as shown in FIG. 7. Operation 420 receives the updates a user has made to one or more of the individual measurements. Operation 425 generates an updated comprehensive safety measurement score based on changes to one or more of the individual safety measurements. Operation 425 applies the stored weights to each of the individual safety measurements to calculate an updated comprehensive safety measurement score. Operation 425 causes the user interactive graphical user interface to present the updated comprehensive safety measurement score to the user to be analyzed for improving safety practices for the hospital.

Although the present technology has been described in detail for the purpose of illustration based on what is currently considered to be the most practical and preferred implementations, it is to be understood such detail is solely for that purpose and the technology is not limited to the disclosed implementations, but, on the contrary, is intended to cover modifications and equivalent arrangements that are within the spirit and scope of the appended claims. For example, it is to be understood the present technology contemplates that, to the extent possible, one or more features of any implementation can be combined with one or more features of any other implementation.

The invention claimed is:

1. A method implemented in a computing system including at least a processor, the method comprising:
receiving comprehensive safety measurement scores, including associated metadata, for multiple hospitals from an external safety rating agency for a time period;
analyzing, by the processor, the metadata to identify hospital identifiers for one or more of the multiple hospitals;
analyzing, by the processor, the metadata to determine (i) individual safety measurements that were used to calculate the comprehensive safety measurement score for a selected hospital identifier representing a hospital, and (ii) a weight associated with each individual safety measurement;
in response to receiving, via a graphical user interface, a first user selection to provide the comprehensive safety measurement score for the hospital, automatically causing the graphical user interface to display the comprehensive safety measurement score for the hospital;
in response to receiving, via the graphical user, a second user selection to provide the individual safety measurements for the hospital determined from the metadata, automatically causing the graphical user interface to display each of the individual safety measurements for the hospital for the time period that were used to calculate the comprehensive safety measurement score;
in response to receiving, via the graphical user, a third user selection to change a selected individual safety measurement from the individual safety measurements for the hospital with a proposed changed value:
initiating a modeling module configured to determine an impact of the proposed changed value by at least:
changing a current value of the selected individual safety measurement to the proposed changed value;
applying the weight associated with the selected individual safety measurement to the proposed changed value;
generating a predicted comprehensive safety measurement score that results based on the proposed changed value by recalculating the comprehensive safety measurement score of the selected hospital with the individual safety measurements that were used to calculate the comprehensive safety measurement score and the proposed changed value; and
displaying, on the graphical user interface, the predicted comprehensive safety measurement score to reflect the predicted impact of the proposed changed value.

2. The method of claim 1, wherein the individual safety measurements comprise multiple of inpatient injuries, infections, medical and medication errors, central line-associated bloodstream infections, catheter-associated urinary tract infections, surgical site infections for colon surgery, MRSA and *C. difficile* infections, falls and trauma, severe pressure injuries, preventable complications from surgery, strong nursing leadership and engagement, computerized physician order entry systems to prevent medication errors, safe medication administration, hand hygiene policies, and the right staffing for the ICU.

3. The method of claim 1, further comprising:
determining, by the processor, which of the individual safety measurements for the hospital are below industry standards.

4. The method of claim 3, further comprising:
automatically causing the graphical user interface display the individual safety measurements for the hospital that are below industry standards.

5. The method of claim 1, further comprising:
determining, by the processor, which of the individual safety measurements have a safety program that can be implemented that would impact the comprehensive safety measurement score for the hospital.

6. The method of claim 5, further comprising:
automatically causing the graphical user interface display in a decision matrix with the individual safety measurements with a safety program as candidates for improvements for the hospital.

7. The method of claim 1, further comprising:
converting the comprehensive safety performance scores from a grade letter to numeric values and determining numeric ranges for each grade letter.

8. The method of claim 7, further comprising:
automatically causing the graphical user interface to display the numeric value for the comprehensive safety performance score for the hospital and the numeric ranges calculated for each grade letter.

9. A method implemented and performed by a computing system including at least a processor, the method comprising:
receiving comprehensive safety measurement scores, including associated metadata, for multiple hospitals from an external resource via a network communication for a time period;
analyzing, by the processor, the metadata to identify hospital identifiers for one or more of the multiple hospitals;
analyzing, by the processor, the metadata to determine:
(i) individual safety measurements that were used to calculate the comprehensive safety measurement score for each hospital identifier representing a hospital,
(ii) a weight associated with each individual safety measurement; and
(iii) location data of each of the multiple hospitals with the comprehensive safety measurement score;
in response to receiving, via a graphical user interface, a first user selection to provide comprehensive safety measurement scores for the multiple hospitals that are in a geographic area based on the location data, automatically causing the graphical user interface to display the comprehensive safety measurement score for each of the multiple hospitals within the geographic area; and
in response to receiving, via the graphical user, a second user selection to change a selected individual safety measurement from the individual safety measurements for a selected hospital in the geographic area with a proposed changed value:
initiating a modeling module configured to determine an impact of the proposed changed value by at least:
changing a current value of the selected individual safety measurement to the proposed changed value;
applying the weight associated with the selected individual safety measurement to the proposed changed value;
generating a predicted comprehensive safety measurement score by recalculating the comprehensive safety measurement score of the selected hospital with the individual safety measurements that were used to calculate the comprehensive safety measurement score including the proposed changed value; and
displaying, on the graphical user interface, the predicted comprehensive safety measurement score to reflect the predicted impact of the proposed changed value.

10. The method of claim 9, further comprising:
determining, by a processor, a hospital system for each of the multiple hospitals with a comprehensive safety measurement score.

11. The method of claim 10, further comprising:
receiving, via a graphical user interface, a user selection to provide comprehensive safety measurements for hospitals within the hospital system.

12. The method of claim 11, further comprising:
automatically causing the graphical user interface to display the comprehensive safety measurement score for each of the hospitals within the hospital system.

13. The method of claim 9, wherein the individual safety measurements comprise multiple of inpatient injuries, infections, medical and medication errors, central line- associated bloodstream infections, catheter-associated urinary tract infections, surgical site infections for colon surgery, MRSA and *C. difficile* infections, falls and trauma, severe pressure injuries, preventable complications from surgery, strong nursing leadership and engagement, computerized physician order entry systems to prevent medication errors, safe medication administration, hand hygiene policies, and staffing for an intensive care unit.

14. A method implemented and performed by a computing system including at least a processor, the method comprising:
receiving comprehensive safety measurement scores, including associated metadata, for multiple hospitals from an external resource via a network communication for a time period;
analyzing, by the processor, the metadata to identify hospital identifiers for one or more of the multiple hospitals;
analyzing, by the processor, the metadata to determine (i) individual safety measurements that were used to calculate the comprehensive safety measurement score for a selected hospital identifier representing a hospital, and (ii) a weight associated with each individual safety measurement;
automatically causing a user interactive graphical user interface to display the comprehensive safety measurement score and the individual safety measurements that were used to calculate the comprehensive safety measurement score for a selected hospital identifier associated with a hospital;
in response to receiving, via the graphical user interface, a user selection to change one or more selected individual measurements of the individual safety measurements for the hospital to one or more proposed changed values:

initiating a modeling module configured to determine an impact of the one or more proposed changed values by at least:
accessing from a database the individual safety measurements and the weights associated with each individual safety measurement;
changing a current value of the one or more selected individual safety measurements to the corresponding one or more sproposed changed value;
applying the weights associated with the one or more selected individual safety measurements to the corresponding one or more proposed changed values;
generating a predicted comprehensive safety measurement score by recalculating the comprehensive safety measurement score of the selected hospital with the individual safety measurements that were used to calculate the comprehensive safety measurement score including the one or more proposed changed values; and
automatically causing the graphical user interface to display the predicted comprehensive safety measurement score for the hospital to reflect the predicted impact of the proposed changed value.

15. The method of claim 14, further comprising:
receiving comprehensive safety measurement scores for multiple hospitals from an external safety rating agency for a time period.

16. The method of claim 14, wherein the change selected by the user is an improvement to the current value of the one or more selected individual safety measurements for the hospital.

17. The method of claim 16, wherein the predicted comprehensive safety measurement score models which changes to the individual safety measurements will have the greatest impact on the comprehensive safety measurement score for the hospital.

18. The method of claim 14, wherein the individual safety measurements comprise multiple of inpatient injuries, infections, medical and medication errors, central line- associated bloodstream infections, catheter-associated urinary tract infections, surgical site infections for colon surgery, MRSA and *C. difficile* infections, falls and trauma, severe pressure injuries, preventable complications from surgery, strong nursing leadership and engagement, computerized physician order entry systems to prevent medication errors, safe medication administration, hand hygiene policies, and the right staffing for an intensive care unit.

19. The method of claim 14, further comprising:
determining, by the processor, which of the individual safety measurements for the hospital are below industry standards; and
automatically causing the graphical user interface to display the individual safety measurements for the hospital that are below industry standards for user selection to change the one or more of the individual safety measurements for the hospital that are below industry standards.

20. The method of claim 14, further comprising:
determining, by a processor, which of the individual safety measurements have a safety program that can be implemented that would impact the comprehensive safety measurement score for the hospital; and
automatically causing the graphical user interface to display in a decision matrix the individual safety measurements with a safety program as candidates for improvements for the hospital for user selection to change the one or more of the individual safety measurements for the hospital that are candidates for improvements the hospital.

* * * * *